United States Patent [19]
Berthiaume et al.

[11] Patent Number: 5,658,309
[45] Date of Patent: Aug. 19, 1997

[54] GUIDEWIRE/INFLATION TUBE LOCKING APPARATUS AND METHOD OF USE

[75] Inventors: William A. Berthiaume, Hudson; Nareak Douk, Lowell, both of Mass.

[73] Assignee: C. R. Bard, Inc., Murray Hill, N.J.

[21] Appl. No.: 431,546

[22] Filed: May 1, 1995

[51] Int. Cl.⁶ .................................................. A61M 29/00
[52] U.S. Cl. ............................................ 606/192; 604/96
[58] Field of Search ........................... 606/194, 192, 606/193; 604/96, 102, 121, 905

[56] References Cited

U.S. PATENT DOCUMENTS

| | | | |
|---|---|---|---|
| 4,860,742 | 8/1989 | Park et al. | 128/303 |
| 5,040,548 | 8/1991 | Yock | 606/194 |
| 5,203,774 | 4/1993 | Gilson et al. | 604/165 |
| 5,269,759 | 12/1993 | Hernandez et al. | 604/96 |
| 5,334,160 | 8/1994 | Ellis | 604/167 |
| 5,387,193 | 2/1995 | Miraki | 606/194 |
| 5,388,590 | 2/1995 | Horrigan et al. | 128/772 |
| 5,484,409 | 1/1996 | Atkinson et al. | 604/96 |
| 5,507,300 | 4/1996 | Mukai et al. | 128/772 |

FOREIGN PATENT DOCUMENTS

| | | |
|---|---|---|
| WO92/06733 | 4/1992 | WIPO . |
| WO93/11750 | 9/1993 | WIPO . |

*Primary Examiner*—Michael Buiz
*Assistant Examiner*—Kevin Truong
*Attorney, Agent, or Firm*—Morgan & Finnegan, L.L.P.

[57] ABSTRACT

A locking apparatus for use with a catheter which includes a catheter body, first and second slidable components which are slidable with respect to the catheter body, and a hub disposed at the proximal end of the catheter body, and a method of using the locking apparatus. The locking apparatus includes a locking device engageable with the hub for locking the first slidable component in a fixed position relative to the hub, and an extension member that is integral with the hub and engageable with the locking device for locking the second slidable component in a fixed position relative to the hub.

19 Claims, 7 Drawing Sheets

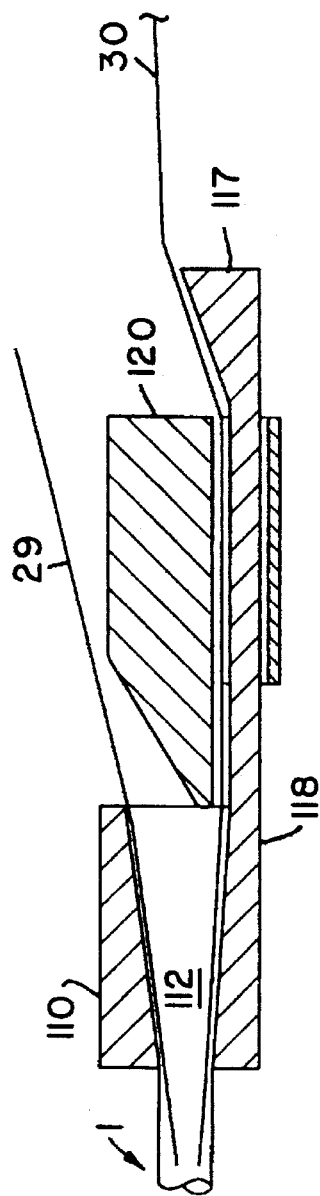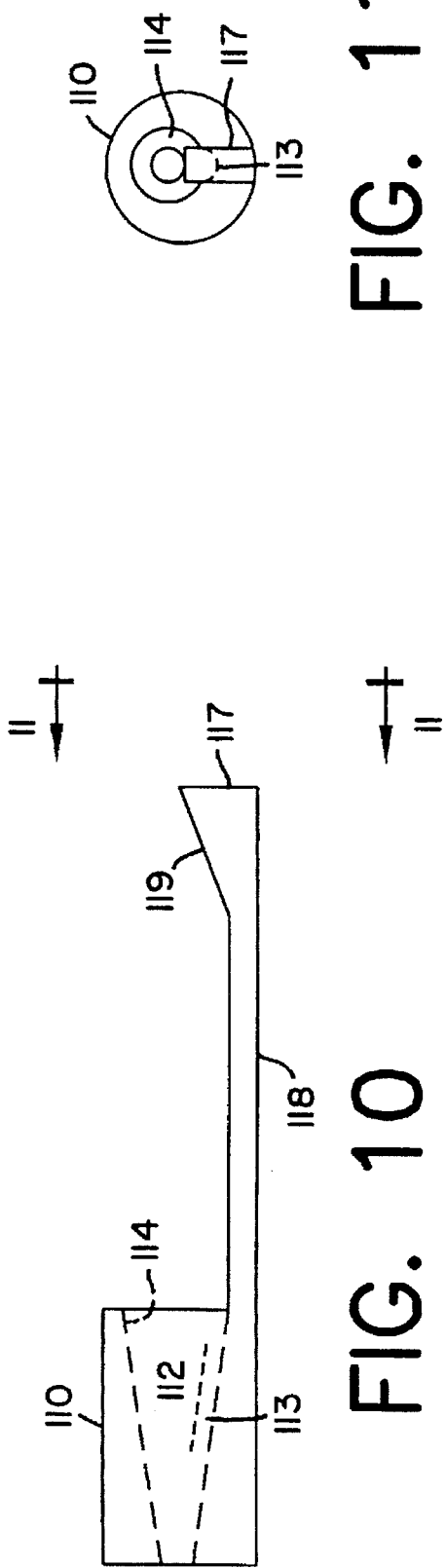
FIG. 9
FIG. 10
FIG. 11

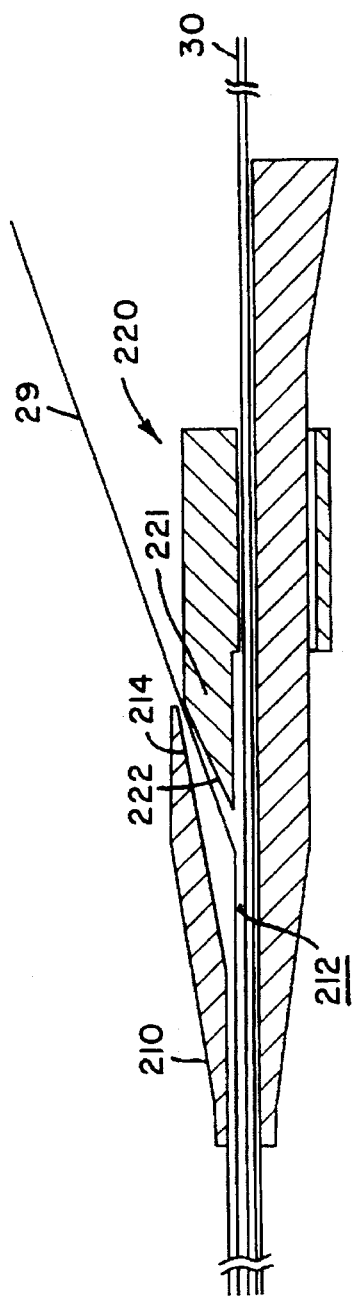
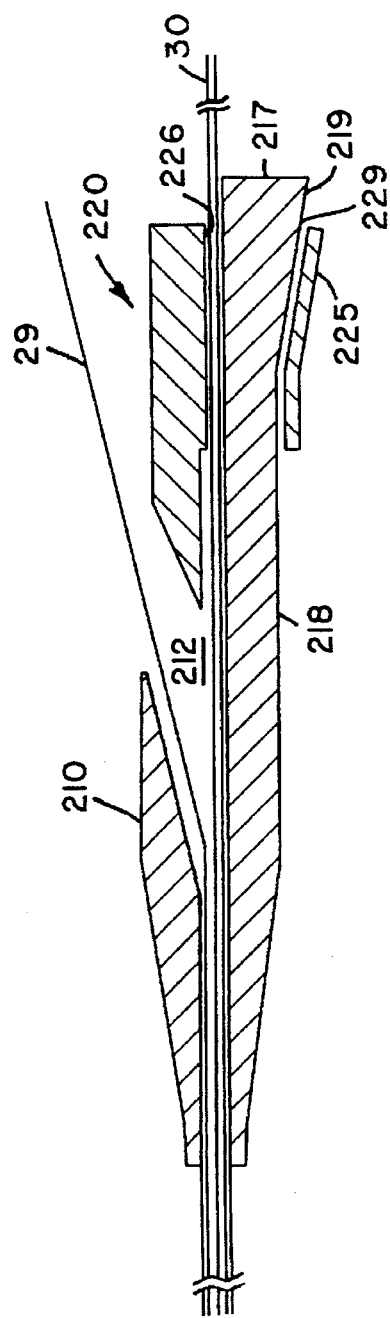

GUIDEWIRE/INFLATION TUBE LOCKING APPARATUS AND METHOD OF USE

FIELD OF THE INVENTION

This invention relates to a device for use with catheters placed in the body of a patient such as in the cardiovascular system.

BACKGROUND OF THE INVENTION

Catheters are placed at various locations within a patient for a wide variety of purposes and medical procedures. For example, one type of catheter is a balloon dilatation catheter which is used in the treatment of a vascular stenosis. Such a catheter has a balloon at its distal end which is intended to be placed, in a deflated condition, within the stenosis, and then inflated while in the stenosis to expand radially the stenosis lumen of the blood vessel. The prior art includes essentially three types of balloon dilatation catheters: "Over-the-wire" catheters, "monorail" catheters and "fixed balloon on a wire" catheters. A fourth type of balloon dilatation catheter, "telescoping" catheters, is the subject of co-pending application Ser. No. 08/198,628 filed Feb. 18, 1994. A telescoping catheter comprises a plurality of telescoping tubes arranged so that the effective "over-the-wire length" of the telescoping catheter can be adjusted.

Typically, the placement of a telescoping catheter involves inserting a guiding catheter into the patient's vasculature. A connector, such as a Tuohy-Borst connector, is disposed at the proximal end of the guiding catheter extending outside of the patient. The connector is opened and a guidewire is advanced through the guiding catheter and the patient's vasculature to the location of the stenosis to be treated. The telescoping catheter, which has a guidewire lumen adapted to receive the guidewire, then is advanced over the guidewire to the stenosis, or, alternatively, the wire and telescoping catheter may be advanced in unison to the stenosis with the guidewire protruding from the distal end of the telescoping catheter.

The telescoping catheter requires the Tuohy-Borst connector to remain open while the catheter and/or guidewire is maneuvered to and from the stenosis. The structure of the telescoping catheter minimizes the amount of backbleeding from the patient's vasculature. Consequently, there is no need for an anti-backbleed device to be disposed at the proximal end of the telescoping catheter. The hub disposed at the proximal end of the telescoping catheter may be a standard hub which is well known in the art.

In the telescoping catheter, the hub is affixed to the proximal end of the proximal telescoping tube. This hub has a central port through which the inflation shaft and the guidewire can be passed. However, the known telescoping catheters do not include a hub that can be used to lock the inflation shaft or the guidewire in a fixed position relative to the hub.

In the performance of a catheterization procedure, it may become necessary to exchange an indwelling telescoping catheter for another catheter having a different sized balloon. With the known telescoping catheters, in order to maintain the guidewire in position across the stenosis, the user must manually grip the guidewire with his fingers at a location just proximal of the hub to prevent the guidewire from being pulled out of the blood vessel with the catheter. In so doing, the user is left with just one free hand with which to remove the indwelling telescoping catheter from the patient.

Furthermore, when the telescoping catheter is loaded onto or removed from the guidewire, it is preferable to maintain the telescoping tubes in the fully retracted position. In the known telescoping catheters, this is accomplished by fully retracting the telescoping tubes and then gripping the inflation tube just proximal of the hub. In so doing, the user is left with just one free hand with which to load the telescoping catheter on to the guidewire and to remove the telescoping catheter from the guidewire.

There is, therefore, a need for a new and improved hub that will allow the guidewire or inflation shaft to be locked in a fixed position-relative to the hub.

In general, it is an object of the present invention to provide a hub for use in a telescoping catheter that is adapted to lock the guidewire or inflation shaft in a fixed position relative to the hub. However, the present invention is not limited to telescoping catheters. The present invention may be readily adapted to be used with other catheter assemblies such as over-the-wire, monorail, and fixed wire catheters.

SUMMARY OF THE INVENTION

In accordance with the invention, a telescoping catheter is provided with an apparatus for locking either the guidewire or inflation shaft relative to the hub disposed at the proximal portion of the catheter.

The telescoping catheter comprises a plurality of telescoping tubes that are slidably mounted on the inflation shaft and are retractably received within each other so that the effective "over-the-wire length" may be adjusted. A hub is disposed at the proximal end of the proximal-most telescoping tube. The hub has a central port through which the inflation shaft and the guidewire are passed. The effective "over-the-wire length" of the telescoping catheter is reduced by withdrawing the inflation shaft proximally from the hub which causes the telescoping tubes to be sequentially retracted within the other telescoping tubes.

The guidewire/inflation shaft locking apparatus comprises an extension member that is integral with the hub and a locking device that is slidably mounted on the inflation shaft proximal of the hub or, in alternative embodiments, slidably mounted on the extension member. The locking device and the central port of the hub may be engaged to lock the guidewire in a fixed position relative to the hub. Alternatively, the locking device and the extension member may be engaged to lock the inflation shaft in a fixed position relative to the hub.

The invention is also adaptable to catheter assemblies other than a telescoping catheter, such as an over-the-wire catheter, a monorail catheter, or a fixed wire-catheter. Unlike the telescoping catheter, the over-the-wire, monorail and fixed wire catheters experience backbleeding. The backbleeding may continue for an extended period of time while the Touhy-Borst connector is open while the catheter and/or guidewire is being maneuvered, often causing complications in the procedure, and even conceivably, resulting in considerable loss of blood from the patient. One known device for controlling backbleeding while positioning an over-the-wire or fixed-wire catheter is described in U.S. Pat. No. 5,203,774 to Gilson et al. This device consists of a rigid sleeve assembled over the shaft of a catheter and shaped to fit into a Tuohy-Borst connector. The sleeve has an external diameter chosen so that when the connector is closed, a seal is formed between the sleeve and the connector, while still allowing for free movement of the catheter shaft in relation to the closed connector and for free movement of the guidewire housed within a lumen of the catheter. Backbleeding is limited to the annulus between the inner diameter of the sleeve and the outer diameter of the catheter, which are chosen to be complementary to minimize backbleeding. A disc-like flange or head is provided at the proximal end of the sleeve to limit axial motion of the sleeve within the connector.

The invention is adaptable to over-the-wire, monorail, fixed wire catheters by adapting the guidewire/inflation shaft locking apparatus to the anti-backbleed hub.

BRIEF DESCRIPTION OF THE DRAWINGS

FIG. 9 is a cross-sectional view of a telescoping balloon catheter with a second embodiment of the hub and guidewire/inflation shaft locking device of the invention with the guidewire/inflation shaft locking device in an unlocked position.

FIG. 10 is a side view of the second embodiment of the hub and extension member.

FIG. 11 is an end view of the hub and extension member when viewed along line 11—11 in FIG. 10.

FIG. 21 is a side view of the third embodiment of the hub and guidewire/inflation shaft locking device with the guidewire/inflation shaft locking device positioned to lock the guidewire to the hub.

FIG. 22 is a side view of the third embodiment of the hub and guidewire/inflation shaft locking device with the guidewire/inflation shaft locking device positioned to lock the inflation shaft to the hub.

DETAILED DESCRIPTION OF THE PREFERRED EMBODIMENTS

It should be noted that while the following description will be specifically in the context of telescoping coronary angioplasty dilatation catheters, the invention is not so limited and is applicable to other catheter assemblies such as over-the-wire and fixed wire catheters.

Figure 1:
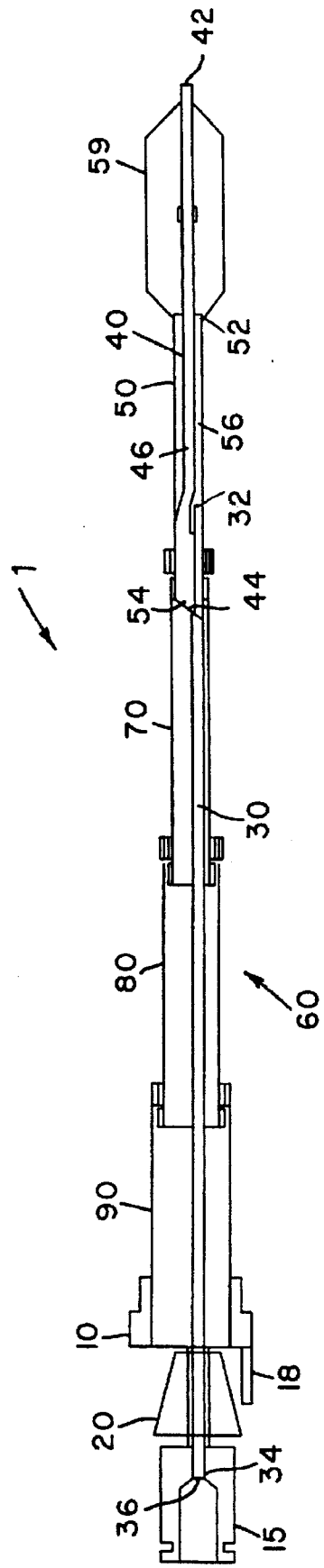
FIG. 1 is a cross-sectional view of a telescoping balloon catheter with a hub and a guidewire/inflation shaft locking device of the invention.

Referring to FIG. 1, the hub 10 and guidewire/inflation shaft locking device 20 of the invention are component parts of a telescoping catheter which is generally designated as 1. The telescoping catheter 1 also includes an elongated inflation shaft 30, a guidewire shaft 40, an extension shaft 50, a balloon member 59, and telescoping portion 60.

The elongated inflation shaft 30 has an open distal end 32 and an open proximal end 34, and an inflation lumen 36 extending therethrough. Preferably, the inflation shaft 30 is formed from stainless steel hypotube in order to lend stiffness and pushability to the catheter 1.

The inflation shaft 30 does not extend for the entire length of catheter 1. The extension shaft 50, which is substantially shorter than the inflation shaft, has an open distal end 52, an open proximal end 54 and an extension lumen 56 extending therethrough. The extension shaft 50 is disposed distal to the inflation shaft 30 and the extension lumen 56 is in fluid communication with and extends the inflation lumen 36 through the extent of the extension shaft 50.

The balloon member 59 is disposed at the distal end of extension shaft 50. The interior of the balloon member 59 is in fluid communication with inflation lumen 36 by way of the extension lumen 56. A fitting 15 is secured to the proximal end of elongated inflation shaft 30 in a suitable manner. Preferably, the fitting 15 is in the form of a female luer fitting. The balloon member 59 is inflated by injecting inflation fluid through the fitting 15, and subsequently deflated by withdrawing the inflation fluid through the fitting 15.

The guidewire shaft 40 has an open distal end 42 and an open proximal end 44, and a guidewire lumen 46 extending therethrough. The guidewire shaft 40 is disposed within the extension shaft 50 and extends through balloon member 59. The proximal end 44 of the guidewire shaft 40 is co-extensive with the proximal end 54 of the extension shaft 50. The distal end of balloon member 59 is affixed to guidewire shaft 40. The distal end of the guidewire shaft 40 extends beyond the distal end of the balloon member 59. The guidewire lumen 46 is sized such that a standard coronary angioplasty guidewire 29 can be slidably received within guidewire lumen 36 (see FIGS. 7 and 8).

The telescoping portion can comprise two or more telescoping tubes which are slidably mounted on the inflation shaft 30 and the extension shaft 50. In the embodiment depicted in FIG. 1, the telescoping portion 60 comprises a first telescoping tube 70, a second telescoping tube 80 and a third telescoping tube 90, all of which are slidably mounted on the inflation shaft 30 and the extension shaft 50. The telescoping tubes are to be formed from a flexible polymer such as polyvinyl chloride, polyethylene, polyethylene terephthalate or, preferably, polyimide. The inner diameter of the third telescoping tube 90 is greater than the outer diameter of the second telescoping tube 80. Similarly, the inner diameter of the second telescoping tube 80 is greater than the outer diameter of the first telescoping tube 70. Thus, the first telescoping tube 70 can be slidably received within the second telescoping tube 80, and both the first and second telescoping tubes 70 and 80, can be slidably received within the third telescoping tube 90. The telescoping tubes are relatively thin in thickness so as not to present too much of a discontinuity on the catheter exterior surface.

A series of stop members may be employed to limit the positioning of the first, second and third telescoping tubes along the inflation shaft 30 and the extension shaft 50 so that the distal ends of the second and third telescoping tubes cannot be positioned distal of the distal end of the first telescoping tube.

Figure 7:
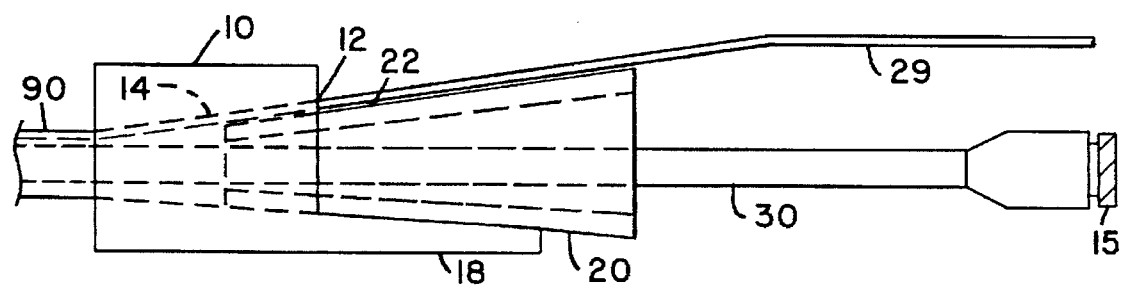
FIG. 7 is a side view of the hub and guidewire/inflation shaft locking device with the guidewire/inflation shaft locking device positioned to lock the guidewire to the hub.
Figure 8:
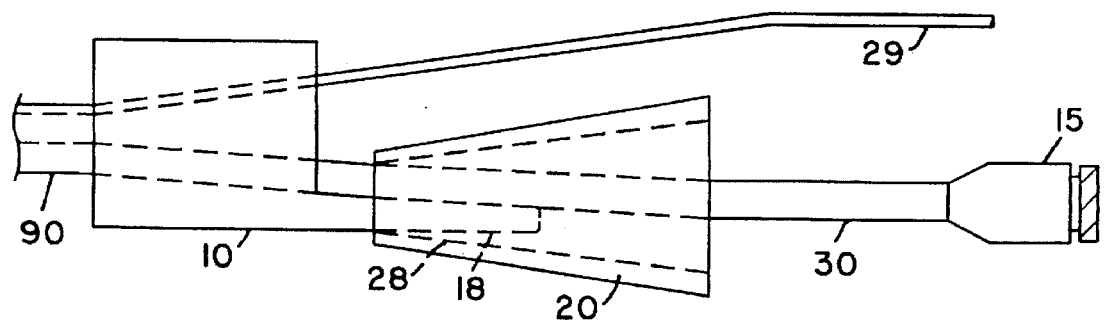
FIG. 8 is a side view of the hub and guidewire/inflation shaft locking device with the guidewire/inflation shaft locking device positioned to lock the inflation shaft to the hub.

A hub 10 is affixed to the proximal end of the proximal-most telescoping tube. In the embodiment depicted in FIG. 1, the hub 10 is affixed to the proximal end of the third telescoping tube 90. Referring to FIGS. 7 and 8, the hub 10 has a central port 12 through which the inflation shaft 30 and the guidewire 29 are passed (see also FIGS. 2 and 3).

When the telescoping portion 60 is in the fully extended position (i.e., the proximal end of the first telescoping tube 70 is located at the distal end of the second telescoping tube 80 and the proximal end of the second telescoping tube is located at the distal end of the third telescoping tube 90, see FIG. 1), the guidewire 29 will be encased by telescoping portion 60 and guidewire shaft 40 as it extends through the hub 10 to the distal end of the catheter 1. The catheter 1, therefore, is an over-the-wire catheter for the full extent of its length when the telescoping portion 60 is in the fully extended position.

The effective "over-the-wire length" of catheter 1 may be reduced by withdrawing the inflation shaft 30 proximally from the hub 10. As a result of the frictional contact between the inner surface of the first telescoping tube 70 and the outer surface of the extension shaft 50, the continued proximally-directed withdrawal of the inflation shaft 30 causes the first telescoping tube 70 to be fully retracted into the second telescoping tube 80. The continued proximally-directed withdrawal of the inflation shaft 30 next causes the second telescoping tube 80 and the indwelling first telescoping tube 70 to be fully retracted into the third telescoping tube 90. The continued proximally-directed withdrawal of the inflation shaft 30 next causes the extension shaft 50 to be retracted into the first telescoping tube 70, which remains located within the second and third telescoping tubes, until the deflated balloon member engages the distal end of the first telescoping tube 70.

Figure 4:
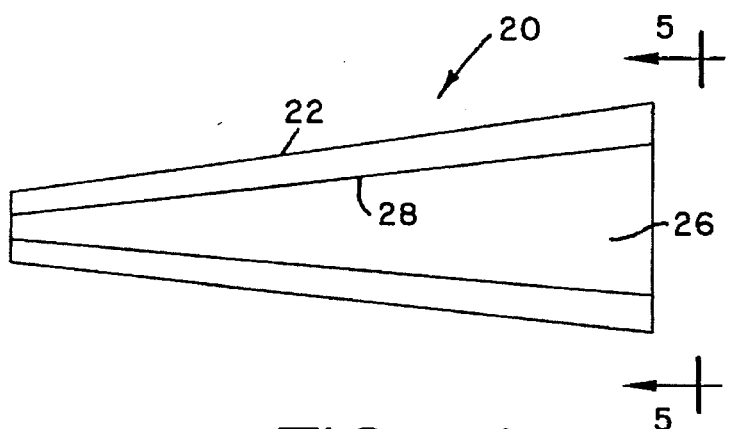
FIG. 4 is a side view of the guidewire/inflation shaft locking device.
Figure 5:
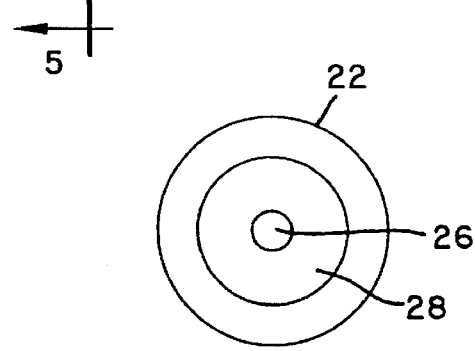
FIG. 5 is an end view of the guidewire/inflation shaft locking device when viewed along line 5—5 in FIG. 4.
Figure 6:
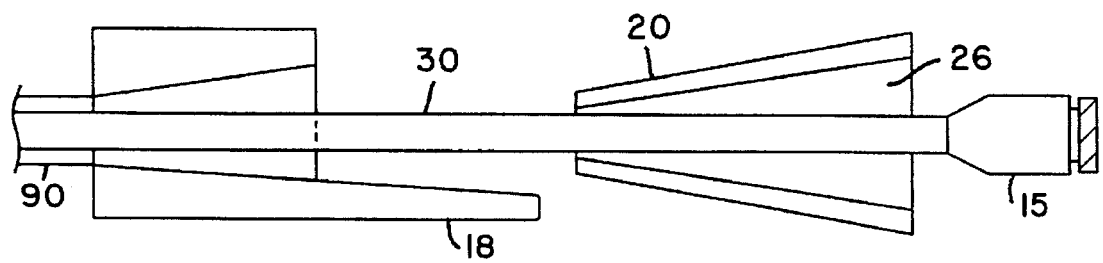
FIG. 6 is a cross-sectional view of the hub and guidewire/inflation shaft locking device with the guidewire/inflation shaft locking device in an unlocked position.

Referring to FIGS. 4 and 5, a locking device 20, which has a locking lumen 26 extending from the distal end to the proximal end thereof, is slidably mounted on the inflation shaft 30 between the hub 10 and the inflation fitting 15. The locking device 20 may be formed from a plastic such as polyethylene or polycarbonate or a metal such as stainless steel. Preferably, the locking device is formed from Kraton® G-2703, which is a saturated styrene rubber available from the Shell Chemical Company of Houston, Tex. The locking device 20 may be positioned so as to lock the guidewire 29 to the hub 10 (see FIG. 7) or, alternatively, the locking device 20 may be positioned so as to lock the inflation shaft 30 to the hub 10 (see FIG. 8).

Figure 2:
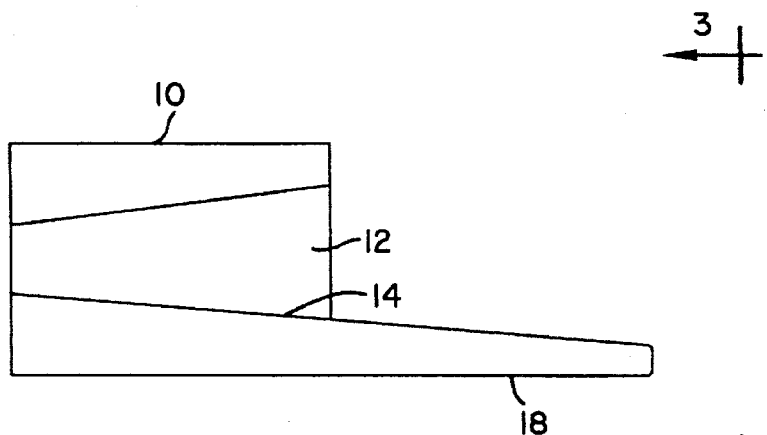
FIG. 2 is a side view of the hub and extension member.
Figure 3:
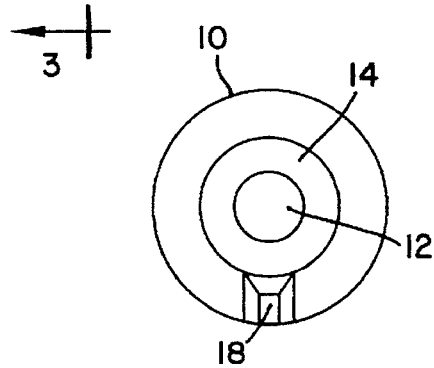
FIG. 3 is an end view of the hub and extension member when viewed along the line 3—3 in FIG. 2.

The locking device 20 is sized and shaped so that the distal portion of the locking device 20 can be slidably received within the proximal portion of the central port 12 extending through the hub 10. Referring to FIG. 2, in a preferred embodiment, the inner wall 14 of the hub 10, which defines the central port 12, is conically-shaped with the diameter of the central port 12 tapering from the proximal end to the distal end of the hub 10. In this preferred embodiment, the locking device 20 is also conically-shaped with the diameter of the outer surface 22 tapering from the proximal end to the distal end of the locking device 20. The taper of the outer surface 22 of locking device 20 and the taper of inner wall 14 of the hub 10 result in an interference fit between the outer surface 22 of the locking device 20 and the inner wall 14 of the hub 10. Referring to FIG. 7, the locking device 20 may be slidably inserted into the central port 12 of the hub 10 with the guidewire 29 extending through central port 12 and lying between the inner wall 14 of hub 10 and the outer surface 22 of the locking device 20, so that this interference fit locks the guidewire 29 in a fixed position relative to the hub 10.

Referring to FIG. 2, extension member 18 is integral with the hub 10 and extends proximally from the proximal end of the hub 10. Preferably, the extension member 18 is formed from the same material as the hub 10, and may be formed from plastic, such as polyethylene or polycarbonate, or metal, such as stainless steel. The thickness of the extension member 18 tapers from its distal end to its proximal end. When the locking device 20 is slidably inserted into the central port 12, the extension member 18 supports the locking device 20. Further, the extension member 18 may be engaged with the locking lumen 26 of the locking device 20 so as to lock the inflation shaft 30 in a fixed position relative to the hub 10.

Referring to FIG. 8, the distal portion of the locking lumen 26 extending through the locking device 20 is sized so that the distal portion of the locking lumen 26 can slide over the proximal portion of the extension member 18. The degree of taper of extension member 18 is such that the combined thickness of the extension member 18 and the inflation shaft 30 exceeds the diameter of the distal portion of locking lumen 26 at a point proximal of the distal end of extension member 18. At that point there will be an interference fit between the inner wall 28 of locking device 20 that forms locking lumen 26 and the inflation shaft 30 and extension member 18. The locking device 20 may be slid over the extension member 18 to that point so that the interference fit between inner wall 28 and the inflation shaft 30 and extension member 18 locks the inflation shaft 30 in a fixed position relative to the hub 10.

Operation and use of the telescoping catheter 1 with hub 10 and locking device 20 may now be briefly described as follows. A guiding catheter (not shown in Figures) is inserted to the coronary artery in a conventional manner. The guidewire 29 may be introduced into the telescoping catheter 1 by a back loading technique and then the combination of the telescoping catheter 1 and guidewire is advanced into the guiding catheter.

Alternatively, the guidewire 29 alone is inserted into the guiding catheter and advanced to the site of the stenosis. Preparatory to loading the catheter 1 onto the indwelling guidewire, the telescoping portion 60 is maneuvered into the fully retracted position so that the effective "over-the-wire length" of the catheter 1 is at a minimum. The distal portion of the catheter 1 is then loaded onto the proximal portion of the indwelling guidewire 29 in a conventional manner while maintaining the telescoping portion 60 in the fully retracted position. In the fully retracted position, the inflation shaft 30 is withdrawn through the hub 10 to the maximum extent possible and the deflated balloon member 59 abuts the distal ends of the fully retracted telescoping tubes. Loading the catheter 1 onto the proximal portion of the indwelling guidewire 29 is a delicate procedure that is best undertaken with the user having two free hands. Locking device 20 may be used to lock the inflation shaft 30 in this position relative to the hub 10 by engaging the locking device 20 and the extension member 18 and thereby effectively locking telescoping portion 60 in the fully retracted position. The user is then free to use both hands to load and forwardly advance the telescoping catheter 1 on the guidewire 29 until the proximal end of the guidewire 29 extends beyond the proximal end of the telescoping catheter 1. At that point, the telescoping portion 60 is unlocked by disengaging the locking device 20 from the extension member 18. The telescoping tubes are extended and advanced into the guiding catheter.

After the catheter 1 is loaded onto the guidewire 29 and advanced into the guiding catheter under either of the above-described alternative methods, the catheter 1 is maneuvered through the tortuous coronary arteries and along the guidewire until the balloon member 59 is located across the stenosis.

As soon as it has been established that the balloon member 59 has been positioned across the stenosis, pressure can be applied by the use of a hand syringe or another pressurizing device well known in the art (not shown in Figures). The inflation of the balloon member 59 can be observed if radiographic contrast liquid is used as the inflation fluid. Inflating the balloon member 59 dilates the stenosis by stretching the coronary artery and simultaneously pressing the stenosis into the artery wall.

Occasionally, the stenosis does not dilate to an acceptable extent. In this instance, the cardiologist will elect to exchange the indwelling catheter for another catheter with a different sized balloon. When replacing a typical over-the-wire catheter, it is necessary that the guidewire protrude from the patient's body by a length greater than the length of the dilatation catheter. With respect to catheter 1, a standard length guidewire is sufficient to effectuate a catheter exchange because the effective "over-the-wire length" of catheter 1 can be reduced by way of the telescoping portion 60.

During catheter exchange procedures, it is desirable maintain the guidewire in position across the stenosis. The user can engage the locking device 20 with the central port 12 of the hub 10 to lock the guidewire 29 in a fixed position relative to the hub 10 and across the stenosis. With one hand, the user grips the fitting 15 and pulls the inflation shaft 30 proximally from the hub 10. As a result of the frictional contact between the inner surface of the first telescoping tube 70 and the outer surface of the extension shaft 50, the continued proximally-directed withdrawal of the inflation shaft 30 causes the first telescoping tube 70 to be fully retracted into the second telescoping tube 80. The continued proximally-directed withdrawal of the inflation shaft 30 next causes the second telescoping tube 80 and the indwelling first telescoping tube 70 to be fully retracted into the third telescoping tube 90. The continued proximally-directed withdrawal of the inflation shaft 30 next causes the extension shaft 50 to be retracted into the first telescoping tube 70, which remains located within the second and third telescoping tubes, until the deflated balloon member 59 engages the distal end of the first telescoping tube 70. In this manner, the effective "over-the-wire length" of catheter 1 will be reduced to the combined length of the third telescoping tube 90 and the balloon member 59. As an example, for a catheter of an overall length of 135 cm and where the length of each telescoping tube is 33 cm and the length of the extension shaft 50 is 36 cm, the effective "over-the-wire length" may be reduced to about 36 cm.

Next, the guidewire 29 is unlocked from the hub 10 by disengaging the locking device 20 from the central port 12 of tile hub 10. With the telescoping portion 60 in the fully retracted position, the catheter 1 is backed-off the guidewire in a conventional manner. The telescoping portion 60 may be locked in the fully retracted position by engaging the locking device 20 with the extension member 18 to lock the inflation shaft 30 in fixed position relative to the hub 10. The minimum effective "over-the-wire" length of catheter is sized to be less than the length of a standard guidewire that protrudes from the patient's body so that an extension wire will not be needed to effect an exchange of catheter 1.

FIGS. 9–15 illustrate a second embodiment of the subject hub and guidewire/inflation shaft locking device. As is the case with the above-discussed embodiment, the hub 110 and guidewire/inflation shaft locking device 120 are component parts of a telescoping catheter 1.

The hub 110 is affixed to the proximal end of the proximal-most telescoping tube. Referring to FIGS. 10 and 11, the hub 110 has a central port 112 through which the inflation shaft 30 and the guidewire 29 are passed. The inner wall 114 of the hub 110, which defines the central port 112, is conically-shaped with the diameter of the central port 112 tapering from the proximal end to the distal end of the hub 110. The inner wall 114 of the hub 110 has a groove 113 that extends distally from the proximal end of the hub 110 to point about mid-way to the distal end of the hub 110. The radius of the groove 113 is sized so that the inflation shaft 30 can be slidably received within the groove 113.

An extension member 118 is integral with the hub 110 and extends proximally from the proximal end of the hub 110. The extension member 118 includes a securing tail 117 that is disposed at the proximal end of the extension member 118. In this embodiment the securing tail 117 is triangular-shaped and oriented upwards with respect to the extension member 118. Preferably, the extension member 118 and securing tail 117 are formed from the same material as the hub 110, which may be formed from plastic, such as polyethylene or polycarbonate, or metal, such as stainless steel.

Figure 12:
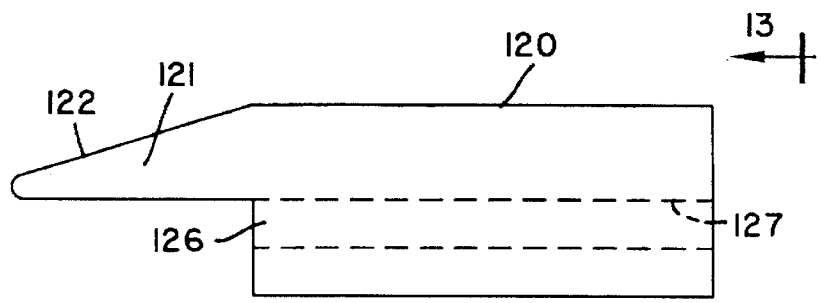
FIG. 12 is a side view of the second embodiment of the guidewire/inflation shaft locking device.
Figure 13:
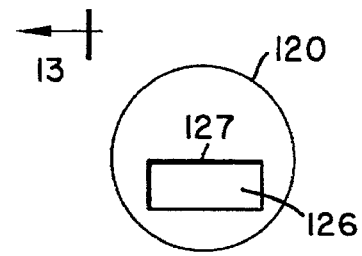
FIG. 13 is an end view of the guidewire/inflation shaft locking device when viewed along line 13—13 in FIG. 12.

Referring to FIGS. 12 and 13, the locking device 120, which is generally cylindrically-shaped with a lumen 126 extending from the distal end to the proximal end, is slidably mounted on the extension member 118 between the hub 110 and the securing tail 117 (see FIG. 9). A tapered guidewire locking portion 121 is disposed at the distal end of the locking device 120. The tapered guidewire locking portion 121, which is integral with the locking device 120, extends distally from the locking device 120 above the lumen 126. The locking device 120 and tapered guidewire locking portion 121 may be formed from a plastic material but is preferably formed from the elastomer such as Kraton® G-2703.

Both the inflation shaft 30 and the guidewire 29 pass through the central port 112 in the hub 110. The lumen 126 in locking device 120 is sized so that when the locking device is slidably mounted on the extension member 118, the inflation shaft 30 extends through the lumen 126 and is slidable therethrough. The guidewire 29 does not extend through the lumen 126 in locking device 120, but rather extends around the locking device 120. The size and shape of the locking device 120 causes the guidewire 29 to pass over the top of the locking device 120.

The locking device 120 is sized and shaped so that the tapered guidewire locking portion 121 can be slidably received within the proximal portion of the central port 112 extending through hub 110. The guidewire locking portion 121 is tapered with its thickness decreasing towards its distal end. The taper of the outer tapered surface 122 of the guidewire locking portion 121 and the taper of the inner wall 114 of the hub 110 result in an interference fit between the outer tapered surface 122 of the locking device 120 and the top portion of the inner wall 114 of the hub 110.

Figure 14:
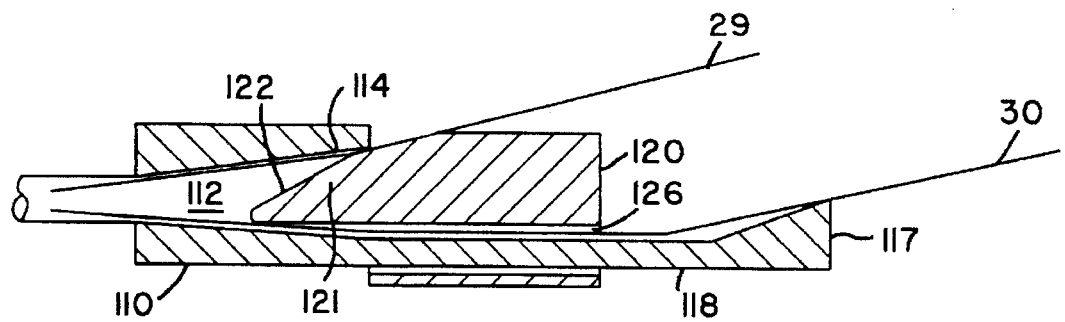
FIG. 14 is a side view of the second embodiment of the hub and guidewire/inflation shaft locking device with the guidewire/inflation shaft locking device positioned to lock tile guidewire to the hub.

Referring to FIG. 14, the locking device 120 may be slidably inserted into the central port 112 of the hub 110 with the guidewire 29 extending through central port 112 and lying between the outer tapered surface 122 of the locking device 120 and the top portion of the inner wall 114 of the hub 110, so that this interference fit locks the guidewire 29 in a fixed position relative to the hub 110. Furthermore, the groove 113 in the inner wall 114 of the hub 110 (see FIG. 10) and the size and shape of the locking device 120 ensure that the inflation shaft 30 can be slidably withdrawn through the hub 110 while the guidewire 29 is locked in position.

Figure 15:
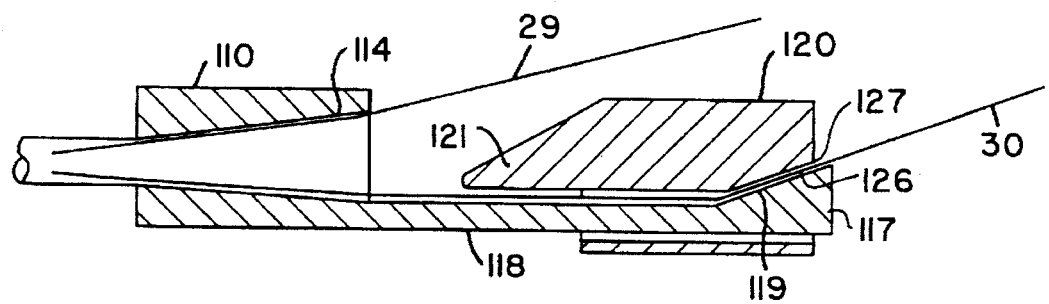
FIG. 15 is a side view of the second embodiment of the hub and guidewire/inflation shaft locking device with the guidewire/inflation shaft locking device positioned to lock the inflation shaft to the hub.

Referring to FIG. 14, the diameter of the lumen 126 through the locking device 120 is substantially less than the maximum height of the triangular-shaped securing tail 117. Referring to FIG. 15, as the locking device 120 is slid proximally along the extension member 118, the proximal portion of the locking device 120 contacts the inclined surface 119 of the triangular-shaped securing tail 117. At that point, the guidewire locking portion 121 is not in contact with the inner wall 114 of the hub 110. In a preferred embodiment, the securing tail 117 is formed from a rigid material and the locking device is formed from a deformable elastomer. In this preferred embodiment, the proximal portion of the locking device 120 in the vicinity of the lumen 126 is somewhat deformed into the shape of the securing tail 117 (see FIG. 15) but an inference fit develops between the inner surface 127 forming lumen 126 through the locking device 120 and the inclined surface 119 of the securing tail 117.

Since the inflation shaft 30 extends through lumen 126 in locking device 120, the inflation shaft 30 will be between the inner surface 127 forming lumen 126 and the inclined surface 119 of the securing tail 117 so that the interference fit will lock the inflation shaft 30 in a fixed position relative to the hub 110. The size of the locking device 120 ensures that the guidewire 29 will not be locked in a fixed position simultaneous with the inflation shaft 30 being locked in a fixed position.

The operation and use of the telescoping catheter 1 with hub 110 and locking device 120 is analogous to that described above with respect to hub 10 and locking device 20.

FIGS. 16-22 illustrate a third embodiment of the subject hub and guidewire/inflation shaft locking device. As is the case with the above-discussed embodiment, the hub 210 and guidewire/inflation shaft locking device 220 are component parts of a telescoping catheter 1.

Figure 17:
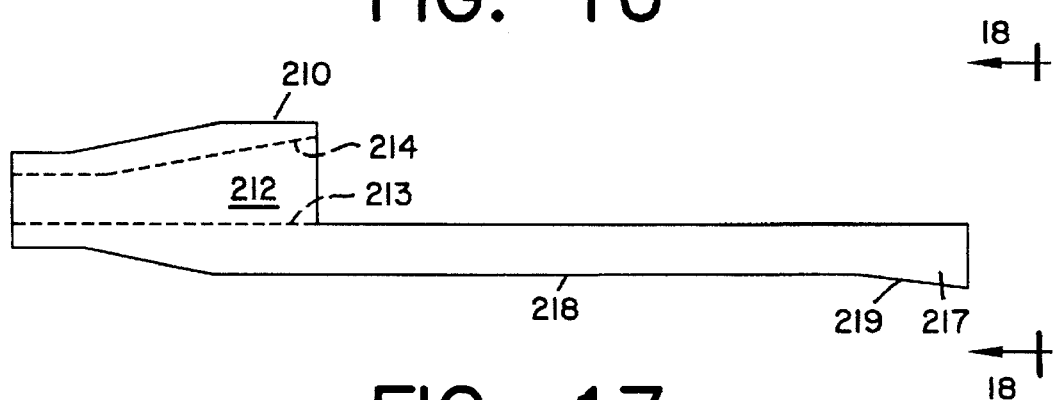
FIG. 17 is a side view of the third embodiment of the hub and extension member.
Figure 18:
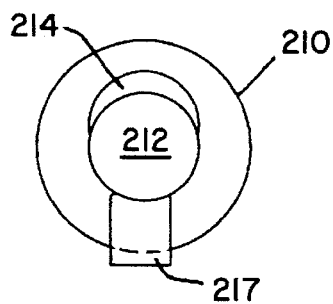
FIG. 18 is an end view of the hub and extension member when viewed along line 18—18 in FIG. 17.

The hub 210 is affixed to the proximal end of the proximal-most telescoping tube. Referring to FIGS. 17-18, the hub 210 has a central port 212 through which the inflation shaft 30 and the guidewire 29 are passed. Unlike the previously discussed embodiments, the interior of the hub 210 is not conically-shaped. Rather, the central port 212 is defined by straight bottom wall portion 213 and tapered top wall portion 214. The top wall portion 214 is tapered so that the diameter of central port 212 at the proximal end of the hub 210 is greater than the diameter of the central port 212 at its distal end.

An extension member 218 is integral with the hub 210 and extends proximally from the proximal end of the hub 210. The extension member 218 includes a securing tail 217 that is disposed at the proximal end of the extension member 218. In the embodiment the securing tail 217 is triangular-shaped and oriented downwards with respect to the extension member 218. Preferably, the extension member 218 and securing tail 217 are formed from the same materials as the hub 210, which may be formed from plastic, such as polyethylene or polycarbonate, or metal, such as stainless steel.

Figure 20:
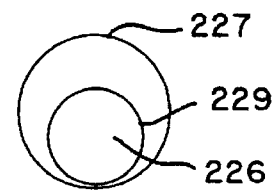
FIG. 20 is an end view of the guidewire/inflation shaft locking device when viewed along line 20—20 in FIG. 19.
Figure 19:
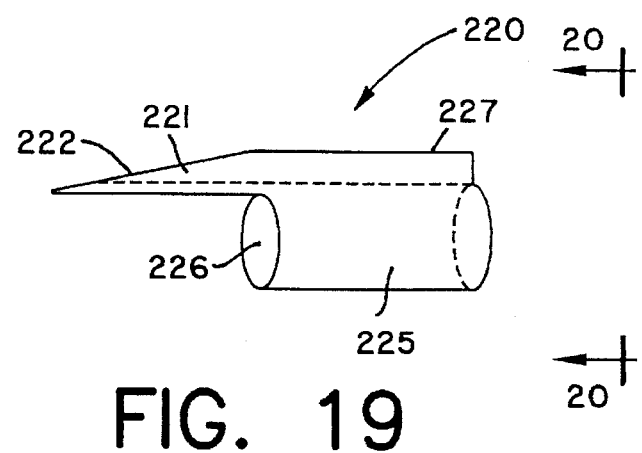
FIG. 19 is a side view of the third embodiment of the guidewire/inflation shaft locking device.

Referring to FIGS. 19-20, the locking device 220 comprises a cylindrically-shaped sliding member 225 with a lumen 226 extending from the distal end to the proximal end, and a locking member 227 disposed on top of and integral with the sliding member 225. The locking member 227 includes a tapered guidewire locking portion 221 which extends distally beyond the distal end of the sliding member 225. The sliding member 225 and locking member 227 may be formed from an elastomer such as Kraton® G-2703. The locking device 220 is slidably mounted on the extension member 218 between the hub 210 and the securing tail 217.

Both the inflation shaft 30 and the guidewire 29 pass through the central port 212 in the hub 210. The lumen 226 in the locking device 220 is sized so that when the locking device 220 is slidably mounted on the extension member 118, the inflation shaft 30 extends through the lumen 226 and is slidable therethrough. The guidewire 29 does not extend through the lumen 226 in locking device 220, but rather extends around the locking device 220. The size and shape of the locking device 220 causes the guidewire 29 to pass over the top of the locking device 220.

The locking device 220 is sized and shaped so that the tapered guidewire locking portion 221 can be slidably received within the proximal portion of the central port 212 extending through hub 210. Referring to FIG. 19, the guidewire locking portion 221 is tapered with its thickness decreasing towards the distal end. The taper of the outer tapered surface 222 of the guidewire locking portion 221 and the taper of the inner top wall portion 214 of the hub 210 result in an interference fit between the outer tapered surface 222 of the locking device 220 and the inner top wall portion 214 of the hub 210.

Referring to FIG. 21, the locking device 220 may be slidably inserted into the central port 212 of the hub 210 with the guidewire 29 extending through central port 212 and lying between the outer tapered surface 222 of the locking device 220 and the inner top wall portion 214 of the hub 210, so that this interference fit locks the guidewire 29 in a fixed position relative to the hub 210. Furthermore, the size and shape of the locking device 220 ensures that the inflation shaft 30 can be slidably withdrawn through the hub 210 while the guidewire 29 is locked in position.

Figure 16:
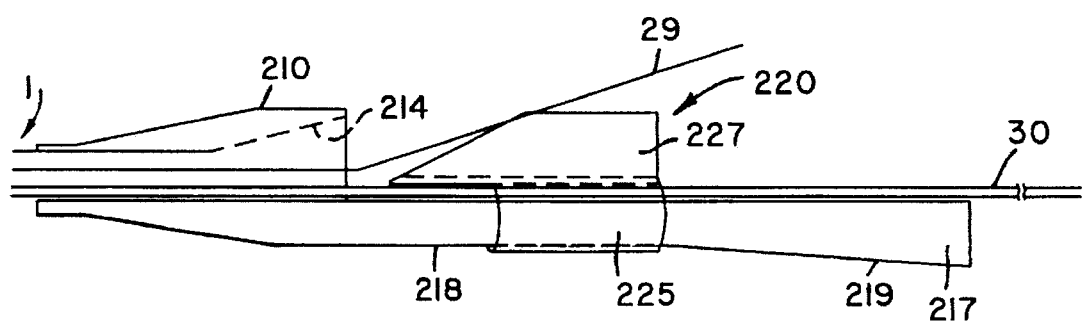
FIG. 16 is a cross-sectional view of a telescoping balloon catheter with a third embodiment of the hub and guidewire/inflation shaft locking device of the invention with the guidewire/inflation shaft locking device in an unlocked position.

Referring to FIG. 16, the diameter of the lumen 226 through the locking device 220 is substantially less than the maximum height of the triangular-shaped securing tail 217. Referring to FIG. 22, as the locking device 220 is slid proximally along the extension member 218, the proximal portion of the locking device 220 contacts the inclined surface 219 of the triangular-shaped securing tail 217, and an inference fit develops between the inner surface 229 forming lumen 226 through the locking device 220 and the inclined surface 219 of the securing tail 217.

Since the inflation shaft 30 extends through the lumen 226 in locking device 220, the inflation shaft 30 will lie between the inner surface 229 forming lumen 226 in locking device 220 and the extension member 218 so that the interference fit will lock the inflation shaft 30 in a fixed position relative to the hub 210. The size of the locking device ensures that the guidewire 29 will not be locked in a fixed position simultaneous with the inflation shaft 30 being locked in a fixed position.

The operation and use of the telescoping catheter 1 with hub 210 and locking device 220 is analogous to that described above with respect to hub 10 and locking device 20.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

What is claimed is:

1. A locking apparatus, in combination with a telescoping catheter which includes an elongated inflation shaft, a plurality of telescoping tubes slidably mounted on said inflation shaft, a guidewire extending the length of said telescoping catheter, and a hub disposed at the proximal end of one of said telescoping tubes and having an inner wall defining a central port through which extend said inflation shaft and said guidewire, said locking apparatus comprising:

locking means engageable with said hub for locking said guidewire in a fixed position relative to said hub; and extension means integral with said hub engageable with said locking means for locking said inflation shaft in a fixed position relative to said hub.

2. A locking apparatus, in combination with a telescoping catheter which includes an elongated inflation shaft, a plurality of telescoping tubes slidably mounted on said inflation shaft, a guidewire extending the length of said telescoping catheter, and a hub disposed at the proximal end of one of said telescoping tubes and having an inner wall defining a central port through which extend said inflation shaft and said guidewire, said locking apparatus comprising:

an extension member integral with said hub; and a locking device having a distal end, a proximal end, an outer wall and an inner wall defining a locking lumen extending between said distal and proximal ends, said locking device slidably mounted on said inflation shaft so that said inflation shaft extends through said locking lumen, said distal end of said locking device engageable with said central port of said hub such that said outer wall of said locking device and said inner wall of said hub lock said guidewire in a fixed position relative to said hub, and said distal end of said locking lumen engageable with said extension member such that said extension member and said inner wall of said locking device lock said inflation shaft in a fixed position relative to said hub.

3. A locking apparatus, in combination with a catheter which includes a catheter body, first and second slidable components which are slidable with respect to the catheter body, and a hub disposed at the proximal end of the catheter body and having an inner wall defining a central port through which extend said first and second slidable components, said locking apparatus comprising:

an extension member integral with said hub and extending proximally from said hub, said extension member having a securing member disposed at its proximal end; and a locking device having a distal end, a proximal end, an outer wall and an inner wall defining a lumen extending between said distal and proximal ends, said locking device slidably mounted on said extension member so that said second slidable component extends through said lumen, said distal end of said locking device engageable with said central port of said hub such that said outer wall of said locking device and said inner wall of said hub lock said first slidable component in a fixed position relative to said hub, and said proximal end of said inner wall defining said lumen in said locking device engageable with said securing member disposed at said proximal end of said extension member such that said securing member and said inner wall of said locking device lock said second slidable component in a fixed position relative to said hub.

4. A locking apparatus, in combination with a telescoping catheter which includes an elongated inflation shaft, a plurality of telescoping tubes slidably mounted on said inflation shaft, a guidewire extending the length of said telescoping catheter, and a hub disposed at the proximal end of one of said telescoping tubes and having an inner wall defining a central port through which extend said inflation shaft and said guidewire, said locking apparatus comprising:

an extension member integral with said hub and extending proximally from said hub, said extension member having a securing member disposed at its proximal end; and a locking device having a distal end, a proximal end, an outer wall and an inner wall defining a lumen extending between said distal and proximal ends, said locking device slidably mounted on said extension member so that said inflation shaft extends through said locking lumen, said distal end of said locking device engageable with said central port of said hub such that said outer wall of said locking device and said inner wall of said hub lock said guidewire in a fixed position relative to said hub, and said proximal end of said inner wall defining said lumen in said locking device engageable with said securing member disposed at said proximal end of said extension member such that said securing member and said inner wall of said locking device lock said inflation shaft in a fixed position relative to said hub.

5. A method for advancing a telescoping catheter with a variable effective over-the-wire length along a standard length guidewire to the stenosis site, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with said hub, and a locking device engageable with said central port of said hub to lock said guidewire in a fixed position relative to said hub and engageable with said extension member to lock said inflation shaft in a fixed position relative to said hub, said method comprising the steps of:

(a) inserting a guiding catheter into a patient's vasculature;

(b) advancing said standard length guidewire, which has a proximal end and a distal end, to across a stenosis site;

(c) maneuvering said first, second and third telescoping tubes to a fully retracted position such that the distal end of said first telescoping tube is located at said distal ends of said second and third tubes;

(d) locking said first, second and third telescoping tubes in said fully retracted position by engaging said locking device with said extension member;

(e) advancing said distal end of said catheter onto said proximal end of said guidewire and forwardly advancing said telescoping catheter until said guidewire proximal end protrudes from said hub;

(f) unlocking said first, second and third telescoping tubes by disengaging said locking device from said extension member; and (g) advancing said first, second and third telescoping tubes until said balloon member is across said stenosis.

6. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with said hub, and a locking device engageable with said central port of said hub to lock said guidewire in a fixed position relative to said hub and engageable with said extension member to lock said inflation shaft in a fixed position relative to said hub, said method comprising the steps of:

(a) advancing said standard length guidewire and telescoping catheter in a patient's vasculature to a stenosis site;

(b) locking said standard length guidewire in position across said stenosis by engaging said locking device with said central port of said hub;

(c) gripping said inflation shaft and withdrawing said inflation shaft through said hub;

(d) continuing to withdraw said inflation shaft so that said first telescoping tube is fully retracted into said second telescoping tube;

(e) continuing to withdraw said inflation shaft so that said second telescoping tube is fully retracted into said third telescoping tube;

(f) continuing to withdraw said inflation shaft so that said extension shaft is fully retracted into said first telescoping tube;

(g) unlocking said standard length guidewire by disengaging said locking device from said central port of said hub;

(h) locking said first, second and third telescoping tubes in position by engaging said locking device with said extension member;

(i) gripping said guidewire at a position one to two inches proximal of said hub with a first hand;

(j) gripping said inflation shaft with a second hand and rearwardly advancing said inflation shaft to said position of said first hand gripping said guidewire;

(k) repeating steps (i)–(j) until said balloon dilatation catheter distal end is withdrawn from said patient; and (l) gripping said guidewire at a position distal of said balloon dilatation catheter distal end and pulling said balloon dilatation catheter off said proximal end of said guidewire.

7. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with said hub, and a locking device engageable with said central port of said hub to lock said guidewire in a fixed position relative to said hub and engageable with said extension member to lock said inflation shaft in a fixed position relative to said hub, said method comprising the steps of:

(a) advancing said standard length guidewire and telescoping catheter in a patient's vasculature to a stenosis site;

(b) locking said standard length guidewire in position across said stenosis by engaging said locking device with said central port of said hub;

(c) gripping said inflation shaft and withdrawing said inflation shaft through said hub;

(d) continuing to withdraw said inflation shaft so that said first telescoping tube is fully retracted into said second telescoping tube;

(e) continuing to withdraw said inflation shaft so that said second telescoping tube is fully retracted into said third telescoping tube;

(f) continuing to withdraw said inflation shaft so that said extension shaft is fully retracted into said first telescoping tube;

(g) unlocking said standard length guidewire by disengaging said locking device from said central port of said hub;

(h) locking said first, second and third telescoping tubes in position by engaging said locking device with said extension member;

(i) gripping said guidewire at a position one to two inches proximal of said hub with a first hand;

(j) gripping said inflation shaft with a second hand and rearwardly advancing said inflation shaft to said position of said first hand gripping said guidewire;

(k) repeating steps (i)–(j) until said balloon dilatation catheter distal end is withdrawn from said patient; and (l) gripping said guidewire at a position distal of said balloon dilatation catheter distal end and pulling said balloon dilatation catheter off said proximal end of said guidewire.

8. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with said hub, and a locking device engageable with said central port of said hub to lock said guidewire in a fixed position relative to said hub and engageable with said extension member to lock said inflation shaft in a fixed position relative to said hub, said method comprising the steps of:

(a) inserting a guiding catheter into a patient's vasculature;

(b) advancing said standard length guidewire, which has a proximal end and a distal end, to across a stenosis site;

(c) maneuvering said first, second and third telescoping tubes to a fully retracted position such that the distal end of said first telescoping tube is located at said distal ends of said second and third tubes;

(d) locking said first, second and third telescoping tubes in said fully retracted position by engaging said locking device with said extension member;

(e) advancing said distal end of said catheter onto said proximal end of said guidewire and forwardly advancing said telescoping catheter until said guidewire proximal end protrudes from said hub;

(f) unlocking said first, second and third telescoping tubes by disengaging said locking device from said extension member; and (g) advancing said first, second and third telescoping tubes until said balloon member is across said stenosis;

(h) locking said standard length guidewire in position across said stenosis by engaging said locking device with said central port of said hub;

(i) gripping said inflation shaft and withdrawing said inflation shaft through said hub;

(j) continuing to withdraw said inflation shaft so that said first telescoping tube is fully retracted into said second telescoping tube;

(k) continuing to withdraw said inflation shaft so that said second telescoping tube is fully retracted into said third telescoping tube;

(l) continuing to withdraw said inflation shaft so that said extension shaft is fully retracted into said first telescoping tube;

(m) unlocking said standard length guidewire by disengaging said locking device from said central port of said hub;

(n) locking said first, second and third telescoping tubes in position by engaging said locking device with said extension member;

(o) gripping said guidewire at a position one to two inches proximal of said hub with a first hand;

(p) gripping said inflation shaft with a second hand and rearwardly advancing said inflation shaft to said position of said first hand gripping said guidewire;

(q) repeating steps (o)–(p) until said balloon dilatation catheter distal end is withdrawn from said patient; and (r) gripping said guidewire at a position distal of said balloon dilatation catheter distal end and pulling said balloon dilatation catheter off said proximal end of said guidewire.

9. A method for advancing a telescoping catheter with a variable effective over-the-wire length along a standard length guidewire to the stenosis site, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with and extending proximally from said hub with a securing member disposed at said proximal end of said extension member, and a locking device engageable with said central port of said hub to lock said guidewire in a fixed position relative to said hub and engageable with said securing member disposed at said proximal end of said extension member to lock said inflation shaft in a fixed position relative to said hub, said method comprising the steps of:

(a) inserting a guiding catheter into a patient's vasculature;

(b) advancing said standard length guidewire, which has a proximal end and a distal end, to across a stenosis site;

(c) maneuvering said first, second tubes to a telescoping tubes to a fully retracted position such that the distal end of said first telescoping tube is located at said distal ends of said second and third tubes;

(d) locking said first, second and third telescoping tubes in said fully retracted position by engaging said locking device with said securing member disposed at said proximal end of said extension member;

(e) advancing said distal end of said catheter onto said proximal end of said guidewire and forwardly advancing said telescoping catheter until said guidewire proximal end protrudes from said hub;

(f) unlocking said first, second and third telescoping tubes by disengaging said locking device from said securing member; and (g) advancing said first, second and third telescoping tubes until said balloon member is across said stenosis.

10. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with and extending proximally from said hub with a securing member disposed at said proximal end of said extension member, and a locking device engageable with said central port of said hub to lock said guidewire in a fixed position relative to said hub and engageable with said securing member disposed at said proximal end of said extension member to lock said inflation shaft in a fixed position relative to said hub, said method comprising the steps of:

(a) advancing said standard length guidewire and telescoping catheter in a patient's vasculature to a stenosis site;

(b) locking said standard length guidewire in position across said stenosis by engaging said locking device with said central port of said hub;

(c) gripping said inflation shaft and withdrawing said inflation shaft through said hub;

(d) continuing to withdraw said inflation shaft so that said first telescoping tube is fully retracted into said second telescoping tube;

(e) continuing to withdraw said inflation shaft so that said second telescoping tube is fully retracted into said third telescoping tube;

(f) continuing to withdraw said inflation shaft so that said extension shaft is fully retracted into said first telescoping tube;

(g) unlocking said standard length guidewire by disengaging said locking device from said central port of said hub;

(h) locking said first, second and third telescoping tubes in position by engaging said locking device with said securing member disposed at said proximal end of said extension member;

(i) gripping said guidewire at a position one to two inches proximal of said hub with a first hand;

(j) gripping said inflation shaft with a second hand and rearwardly advancing said inflation shaft to said position of said first hand gripping said guidewire;

(k) repeating steps (i)–(j) until said balloon dilatation catheter distal end is withdrawn from said patient; and (l) gripping said guidewire at a position distal of said balloon dilatation catheter distal end and pulling said balloon dilatation catheter off said proximal end of said guidewire.

11. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with and extending proximally from said hub with a securing member disposed at said proximal end of said extension member, and a locking device engageable with said central port of said hub to lock said guidewire in a fixed position relative to said hub and engageable with said securing member disposed at said proximal end of said extension member to lock said inflation shaft in a fixed position relative to said hub, said method comprising the steps of:

(a) advancing said standard length guidewire and telescoping catheter in a patient's vasculature to a stenosis site;

(b) locking said standard length guidewire in position across said stenosis by engaging said locking device with said central port of said hub;

(c) gripping said inflation shaft and withdrawing said inflation shaft through said hub;

(d) continuing to withdraw said inflation shaft so that said first telescoping tube is fully retracted into second telescoping tube;

(e) continuing to withdraw said inflation shaft so that said second telescoping tube is fully retracted into said third telescoping tube;

(f) continuing to withdraw said inflation shaft so that said extension shaft is fully retracted into said first telescoping tube;

(g) unlocking said standard length guidewire by disengaging said locking device from said central port of said hub;

(h) locking said first, second and third telescoping tubes in position by engaging said locking device with said securing member disposed at said proximal end of said extension member;

(i) gripping said guidewire at a position one to two inches proximal of said hub with a first hand;

(j) gripping said inflation shaft with a second hand and rearwardly advancing said inflation shaft to said position of said first hand gripping said guidewire;

(k) repeating steps (i)–(j) until said balloon dilatation catheter distal end is withdrawn from said patient; and (l) gripping said guidewire at a position distal of said balloon dilatation catheter distal end and pulling said balloon dilatation catheter off said proximal end of said guidewire.

12. A method for advancing a telescoping catheter with a variable effective over-the-wire length along a standard length guidewire to the stenosis site where the catheter is an over-the-wire catheter over the full extent of its length and rapidly exchanging said catheter without making use of an exchange guidewire by reducing the effective over-the-wire length of said catheter, said telescoping catheter having an elongated inflation shaft having open proximal end distal ends and a longitudinal inflation lumen extending therethrough, an extension shaft disposed distal to said inflation shaft, said extension shaft having open proximal and distal ends and a lumen extending therethrough that is in fluid communication with and extends said inflation lumen through the extent of said extension shaft, a guidewire shaft having open proximal end, distal ends and a guidewire lumen extending therethrough, said proximal end of said guidewire shaft being coextensive with said proximal end of said extension shaft, said guidewire shaft extending through said extension shaft lumen and said guidewire shaft distal end extending distal of said extension shaft distal end, an inflatable balloon having a distal end and a proximal end, said balloon proximal end sealingly affixed to said distal end of said extension shaft, said balloon distal end sealingly affixed to said guidewire shaft about said guidewire shaft distal end and the interior of said balloon in fluid communication with said inflation lumen, a first telescoping tube slidably mounted on said inflation shaft and said extension shaft so as to be extendable over at least a portion of a guidewire extending proximally from said guidewire lumen, said first telescoping tube having an inner diameter sized to permit said extension shaft to be retracted into said first telescoping tube but smaller than said balloon when deflated so that said balloon cannot be retracted into said first telescoping tube, a second telescoping tube slidably mounted on said inflation shaft and said extension shaft so as to be extendable over at least a portion of a guidewire extending proximally from said guidewire lumen, said second telescoping tube having an inner diameter sized to permit said first telescoping tube to be retracted into said second telescoping tube, a third telescoping tube slidably mounted on said inflation shaft and said extension shaft so as to be extendable over at least a portion of a guidewire extending proximally from said guidewire lumen, said third telescoping tube having an inner diameter sized to permit said second telescoping tube to be retracted into said third telescoping tube, and said third telescoping tube operatively associated with said first and second telescoping tubes so that the effective over-the-wire length of said balloon dilatation catheter will be reduced as a result of a withdrawal of said inflation shaft from a patient's body, a hub disposed at said proximal end of said third telescoping tube, said hub has a central port so that said inflation shaft and said guidewire can be extended through said hub, an extension member integral with and extending proximally from said hub with a securing member disposed at said proximal end of said extension member, and a locking device engageable with said central port of said hub to lock said guidewire in a fixed position relative to said hub and engageable with said securing member disposed at said proximal end of said extension member to lock said inflation shaft in a fixed position relative to said hub, said method comprising the steps of:

(a) inserting a guiding catheter into a patient's vasculature;

(b) advancing said standard length guidewire, which has a proximal end and a distal end, to across a stenosis site;

(c) maneuvering said first, second and third telescoping tubes to a fully retracted position such that the distal end of said first telescoping tube is located at said distal ends of said second and third tubes;

(d) locking said first, second and third telescoping tubes in said fully retracted position by engaging said locking device with said securing member disposed at said proximal end of said extension member;

(e) advancing said distal end of said catheter onto said proximal end of said guidewire and forwardly advancing said telescoping catheter until said guidewire proximal end protrudes from said hub;

(f) unlocking said first, second and third telescoping tubes by disengaging said locking device from said securing member; and (g) advancing said first, second and third telescoping tubes until said balloon member is across said stenosis;

(h) locking said standard length guidewire in position across said stenosis by engaging said locking device with said central port of said hub;

(i) gripping said inflation shaft and withdrawing said inflation shaft through said hub;

(j) continuing to withdraw said inflation shaft so that said first telescoping tube is fully retracted into said second telescoping tube;

(k) continuing to withdraw said inflation shaft so that said second telescoping tube is fully retracted into said third telescoping tube;

(l) continuing to withdraw said inflation shaft so that said extension shaft is fully retracted into said first telescoping tube;

(m) unlocking said standard length guidewire by disengaging said locking device from said central port of said hub;

(n) locking said first, second and third telescoping tubes in position by engaging said locking device with said securing member disposed at said proximal end of said extension member;

(o) gripping said guidewire at a position one to two inches proximal of said hub with a first hand;

(p) gripping said inflation shaft with a second hand and rearwardly advancing said inflation shaft to said position of said first hand gripping said guidewire;

(q) repeating steps (o)–(p) until said balloon dilatation catheter distal end is withdrawn from said patient; and (r) gripping said guidewire at a position distal of said balloon dilatation catheter distal end and pulling said balloon dilatation catheter off said proximal end of said guidewire.

13. A locking device in combination with a catheter and a guidewire which is slidable with respect to said catheter, said catheter includes a catheter body having a distal end and a proximal end, an elongated slidable portion which is slidable with respect to said catheter body, and a hub disposed at the proximal end of said catheter body, said locking device comprising:

a first locking surface engageable with said hub for locking said guidewire in a fixed position relative to said hub while said elongated slidable portion remains slidable with respect to said catheter body; and a second locking surface engageable with said hub for locking said elongated slidable portion in a fixed position relative to said hub while said guidewire remains slidable with respect to said catheter.

14. A locking apparatus, in combination with a catheter and a guidewire which is slidable with respect to said catheter, said catheter includes a catheter body having a distal end and a proximal end, an elongated slidable portion which is slidable with respect to said catheter body, and a hub disposed at said proximal end of said catheter body, said hub having an inner wall defining a central port through which extend said guidewire and elongated slidable portion, said locking apparatus comprising:

an extension member integral with said hub; and a locking device having a distal end, a proximal end, an outer first locking surface and an inner second locking surface defining a locking lumen extending between said distal and proximal ends, said locking device slidably mounted on said elongated slidable portion so that said elongated slidable portion extends through said locking lumen, said locking device engageable with said central port of said hub such that said first locking surface engages with said inner wall of said hub to lock said guidewire in a fixed position relative to said hub while said elongated slidable portion remains slidable with respect to said catheter body, and said locking device engageable with said hub such that said second locking surface engages with said extension member to lock said elongated slidable portion in a fixed position relative to said hub while said guidewire remains slidable with respect to said catheter.

15. The locking apparatus defined in claim 14 wherein said extension member extends proximally from said hub.

16. The locking apparatus defined in claim 15 wherein said extension member supports said locking device when said locking device is engaged with said central port of said hub.

17. A locking device in combination with a catheter and a guidewire which is slidable with respect to said catheter, said catheter includes a catheter body having a distal end and a proximal end, an elongated portion, and a hub disposed at the proximal end of said catheter body, said locking device comprising:

a locking surface slidably engageable with said hub for locking said guidewire in a fixed position relative to said hub; and sliding means for slidingly mounting said locking surface on said elongated portion so that said locking surface is slidable with respect to said hub.

18. A locking device in combination with a catheter and a guidewire which is slidable with respect to said catheter, said catheter includes a catheter body having a distal end and a proximal end, an elongated slidable portion which is slidable with respect to said catheter body, and a hub disposed at the proximal end of said catheter body, said hub having an inner wall defining a central port through which extend said guidewire and elongated slidable portion, said locking device comprising:

a locking surface slidably engageable with said inner wall of said hub to lock said guidewire in a fixed position relative to said hub while said elongated slidable portion remains slidable with respect to said catheter body; and sliding means for slidingly mounting said locking surface on said elongated slidable portion so that said locking surface is slidable with respect to said hub.

19. A locking device in combination with a telescoping catheter and a guidewire which is slidable with respect to said telescoping catheter, said telescoping catheter includes an elongated inflation shaft, a plurality of telescoping tubes slidably mounted on said inflation shaft, and a hub disposed at the proximal end of one of said telescoping tubes and having an inner wall defining a central port through which extend said inflation shaft and said guidewire, said locking device comprising:

a locking surface slidably engageable with said inner wall of said hub to lock said guidewire in a fixed position relative to said hub; and sliding means for slidingly mounting said locking surface on said inflation shaft so that said locking surface is slidable with respect to said hub.

* * * * *